United States Patent [19]

Dickakian

[11] Patent Number: 5,132,225
[45] Date of Patent: * Jul. 21, 1992

[54] METHOD FOR CONTINUAL MONITORING AND TREATING A HYDROCARBON OIL STREAM

[75] Inventor: Ghazi B. Dickakian, Kingwood, Tex.

[73] Assignee: Exxon Chemical Patents Inc., Linden, N.J.

[*] Notice: The portion of the term of this patent subsequent to Jun. 21, 2005 has been disclaimed.

[21] Appl. No.: 715,329

[22] Filed: Jun. 14, 1991

Related U.S. Application Data

[63] Continuation of Ser. No. 111,885, Oct. 23, 1987, abandoned, which is a continuation-in-part of Ser. No. 849,600, Apr. 8, 1986, Pat. No. 4,762,797, and Ser. No. 24,730, Mar. 11, 1987, Pat. No. 4,781,893, which is a continuation-in-part of Ser. No. 910,910, Sep. 24, 1986, Pat. No. 4,781,892, which is a continuation-in-part of Ser. No. 830,386, Feb. 18, 1986, Pat. No. 4,752,587, which is a continuation-in-part of Ser. No. 723,598, Apr. 15, 1985, Pat. No. 4,751,187.

[51] Int. Cl.⁵ ............................................. G01N 30/90
[52] U.S. Cl. ...................... 436/60; 73/61.52; 73/53.05; 436/139; 436/162; 208/48 AA; 208/309
[58] Field of Search ............... 436/53, 60, 139, 162; 73/61.1 C, 61.4, 64, 61.2; 208/48 AA, 309

[56] References Cited

U.S. PATENT DOCUMENTS

| | | | |
|---|---|---|---|
| 4,671,103 | 6/1987 | Dickakian | 73/61.1 C |
| 4,751,187 | 6/1988 | Dickakian | 436/139 |
| 4,752,587 | 6/1988 | Dickakian | 436/139 |
| 4,762,797 | 8/1988 | Dickakian | 436/60 |
| 4,781,892 | 11/1988 | Dickakian | 436/60 |
| 4,781,893 | 11/1988 | Dickakian | 422/69 |
| 4,853,337 | 8/1989 | Dickakian | 436/55 |

OTHER PUBLICATIONS

Selucky et al., "Thin-Layer Chromatography As An Alternative to SARA Analysis of Coal Derived Liquids", Marcel Dekker Inc. ©1985.

Poirier et al., "Rapid Method of Determination of Malthene and Asphaltene Content in Bitumen, Heavy Oils and Synthetic Fuels" by Pyrolysis TLC., ©1982.

Ray et al., The Application of the Iatroscan TLC Technique to the Analysis of Fossil Fuels.

Poirier et al., "Thin Layer Chromatographic Method for Determination of Asphaltene Content in Crude Oils and Bitumens", Energy Sources, vol. 7, No. 2, ©1983.

Dikakian, "Asphaltene Precipitation Primary Crude Exchanger Fouling Mechanism", Oil & Gas Journal, ©1988.

Primary Examiner—James C. Housel
Assistant Examiner—David Redding
Attorney, Agent, or Firm—R. L. Graham

[57] ABSTRACT

Samples of a petroleum oil stream (e.g. crude oil feed stream to a refinery) are continually monitored to determine incompatible asphaltenes therein and the rate of antifoulant is adjusted in response to changes in the level of incompatible asphaltenes. The method of the present invention employs thin layer chromatographic films for separating incompatible asphaltenes and for measuring an optical property indicative of the incompatible asphaltenes, and for varying antifoulant addition in response to changes of the optical property measured.

4 Claims, 2 Drawing Sheets

METHOD FOR CONTINUAL MONITORING AND TREATING A HYDROCARBON OIL STREAM

CROSS REFERENCE

This is a continuation of application U.S. Ser. No. 111,885, filed Oct. 23, 1987 (now abandoned), which is a continuation-in-part of U.S. Ser. No. 849,600, filed Apr. 8, 1986, (now U.S. Pat. No. 4,762,797), and U.S. Ser. No. 024,730, filed Mar. 11, 1987, (now U.S. Pat. No. 4,781,893), which is a continuation-in-part of U.S. Ser. No. 910,910, filed Sep. 24, 1986 (now U.S. Pat. No. 4,781,892), which is a continuation-in-part of U.S. Ser. No. 830,386, filed Feb. 18, 1986 (now U.S. Pat. No. 4,752,587), which is a continuation-in-part of U.S. Ser. No. 723,598, filed Apr. 15, 1985 (now U.S. Pat. No. 4,751,187).

BACKGROUND OF THE INVENTION

1. Field of the Invention

The present invention relates to a method and apparatus for treating petroleum oils e.g., crudes and residues, with antifoulants to reduce fouling of heated metal surfaces such as heat exchangers. In one aspect, it relates to a method and apparatus for monitoring fouling tendency of hydrocarbon oil stream at frequent time intervals and to adjust antifoulant treating rates in response thereto.

2. Related Art

Different crude oils have different precipitating and fouling characteristics with regard to heated metal surfaces in refinery equipment. The problem of predicting the offending substances in a particular crude oil which foul heat exchanger equipment in oil refineries and petrochemical plants has been virtually unresolved. Fouling of hydrocarbon streams, consisting of carbonaceous deposits on heat exchanger surfaces, leads to a blockage of flow and a decrease in heat transfer. Both resulting conditions severely reduce efficiency in the processing of the crude oil and other liquid hydrocarbons. If it can be predicted which fractions of the crude oils are troublesome, measures can be taken in advance to prevent this fouling by either removing the offending substances causing the deleterious deposits, or by adding antifouling additives to the flow stream to reduce deposit formation. Therefore, it would be most desirable to be able to predict these fouling substances.

All crude oils are composed of two major components, a low molecular weight oil fraction (aromatic and/or saturates), and a high molecular weight fraction insoluble in paraffinic solvents. This fraction is called $C_7$-asphaltenes. As used herein the term "asphaltenes" refers to these high molecular weight paraffinic insoluble asphaltenes. Asphaltenes are characterized by a high average molecular weight (about 1000 and up to 5,000) and very broad molecular weight distribution (up to 10,000) and high coking tendency.

Fouling in crude oil heat exchangers is a function of crude oil composition, presence of asphaltenes and inorganic materials, process pressure and the temperature of the metal surface. Although there are a number of mechanisms which contribute to crude oil fouling, tests have shown asphaltene/oil incompatibility is a major contributing factor.

There are a number of methods available for determining the rates of fouling of hydrocarbon streams. Conceptually, they are all similar in that they attempt to measure the change in heat transferred from a heated surface to a test fluid.

One approach is to use a test unit which is configured to allow measurement of the fluid temperature at the exit of the heat exchanger while the metal temperature of the heated tube is controlled, which is generally referred to as the Thermal Fouling Tester (TFT). This configuration provides for close simulation of refinery and petrochemical plant heat exchanger operations and provides for measurement of the significant effect of fouling which is indicated by the reduction of heat transfer. The test unit provides for a thermal fouling evaluation of the crude oil in an accelerated test which is designed to reproduce the fouling problem experienced in a refinery over several months. Acceleration is provided by carrying out test operating temperatures higher than those in a particular refinery unit, so that the prospective level of fouling can be produced in a reasonable period of time (usually 3-4 hours). Heat transfer data is obtained by holding the heater tube at a constant temperature, while measuring the change in the liquid outlet temperature. As fouling progresses, i.e., a carbonaceous deposit builds up on the heater tube surface, a decrease in the fluid outlet temperature results when using a constant outlet liquid temperature operation. The change in liquid outlet temperature with time provides the basic heat data required for comparative evaluation of untreated material and additive-treated material. The rate of change in outlet liquid temperature versus time shows relative fouling tendencies. The duration of this test is usually three hours or longer. In practice in the laboratory, the turnaround for a single sample in this equipment is about one day to obtain results. And one test unit will generally produce about 200 test in a year. However, refinery feeds and streams change constantly and multiple test, e.g., 10 to 50 or 60 per day may be required for full evaluation and control of the refinery operations. The TFT tests are based on the fouling tendency of the hydrocarbon oil under actual fouling conditions and are not predictive.

Because of the length of time to carry out these actual performance tests, the treatment of a stream generally is not responsive to frequent changes in fouling tendency of hydrocarbon oils. Normally, the treatment rate for a particular hydrocarbon oil is established and not changed for long periods of time. This either results in wasteful over-treatment or risky under-treatment because of changes in the fouling tendency of the hydrocarbon stream are not detected. There has not been a method or apparatus for continually monitoring at frequent time intervals the fouling tendency of a hydrocarbon oil stream flowing into the refinery and adjusting treatment rates in response thereto.

SUMMARY OF THE INVENTION

The method of the present invention involves determining the fouling tendency of a petroleum oil stream; adding an antifoulant based on said determination; monitoring the incompatible asphaltene in the stream at frequent time intervals, and adjusting the rate of antifoulant addition in response to changes in the incompatible asphaltenes as determined in the monitoring step. The monitoring step may be performed by the following methods: (a) thin layer chromatography as described in copending U.S. patent application Ser. No. 723,598, filed Apr. 15, 1985, now U.S. Pat. No. 4,751,187, and U.S. patent application Ser. No. 830,386, filed Feb. 18, 1986, now U.S. Pat. No. 4,752,587; U.S.

patent application Ser. No. 910,910, filed Sep. 24, 1986, now U.S. Pat. No. 4,781,892, and U.S. patent application Ser. No. 024,730, filed Mar. 11, 1987, now U.S. Pat. No. 4,781,893; (b) high performance liquid chromatography as described in U.S. Pat. No. 4,671,103; (c) determining the ratio of aromatics to asphaltenes as described in copending U.S. patent application Ser. No. 849,600, filed Apr. 8, 1986, now U.S. Pat. No. 4,762,797; or (d) any other method which provides an indication of the petroleum oil to foul (i.e measuring a property of the oil indicative of incompatible asphaltenes therein). The disclosures of said five U.S. patent applications and one patent are incorporated herein by reference. The term "incompatible asphaltenes" as used herein refers to the insolubility of asphaltenes in the petroleum oil and, as described in detail below, is a function of aromatic content of the petroleum oil. The term "petroleum oil" as used herein includes crude oils, petroleum residues, hydrocarbons, heteroatom compounds normally found as constituents in crude oils and the fractions derived from any of the above.

The apparatus of the present invention comprises means for continually, and preferably automatically, withdrawing a sample from the hydrocarbon oil stream at frequent time intervals; means for determining the tendency of said sample to foul by measuring a property of the sample indicative of incompatible asphaltenes in the sample; and means for automatically adjusting the rate of antifoulant introduced into said stream responsive to changes in said property.

It is important to the present invention that the property or characteristic (e.g. ratio of aromatic/asphaltenes) of the petroleum oil in question is a physical and/or chemical property of the oil and is not a performance property such as that determined by the TFT. The invention thus permits predicting fouling tendency without time consuming performance testing.

DESCRIPTION OF THE PREFERRED EMBODIMENTS

Method

Figure 1:
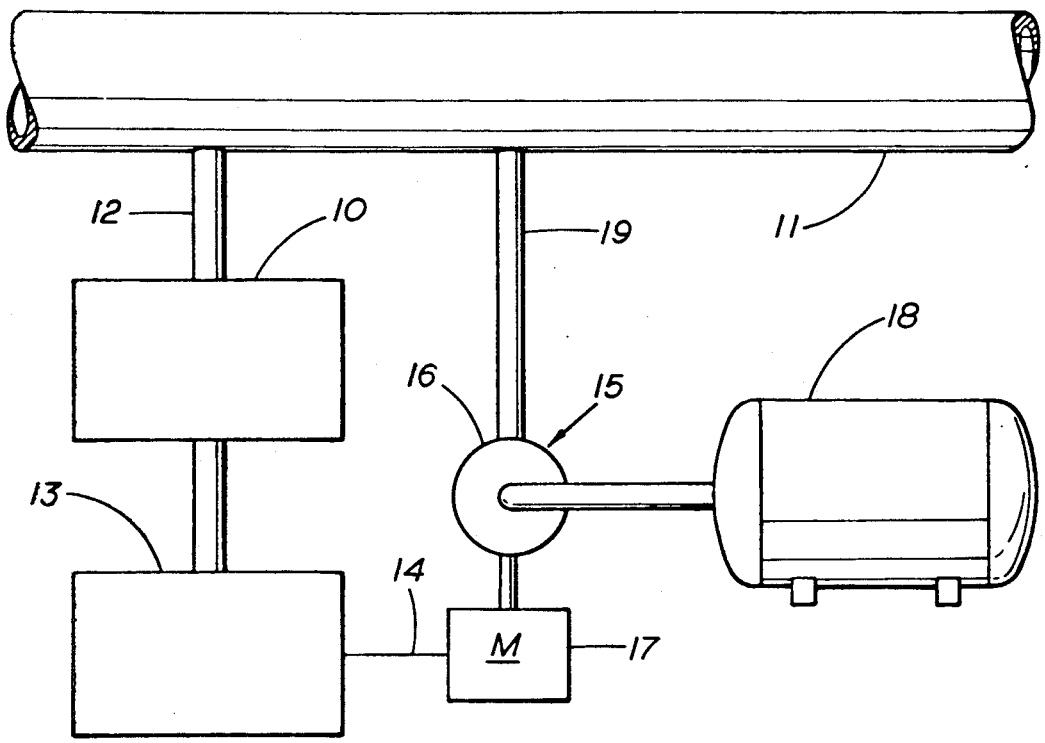
FIG. 1 is a process flow diagram illustrating the process of the present invention.

In one aspect, the present invention provides a method for continually monitoring a property of a petroleum oil stream indicative of the fouling tendency of the oil in refinery operations at frequent time intervals to optimize the addition of antifoulant. The property indicative of the fouling tendency is based on the incompatibility of the asphaltenes in the petroleum oil. This property may be determined by processes referred to herein as (A.) Ratio of Aromatics to Asphaltenes and (B.) Thin Layer Chromatography. Each of these methods are described in detailed below.

A. Ratio of Aromatics to Asphaltenes

The weight ratio of the total aromatics (polar + neutral) to asphaltenes in a petroleum oil provides an accurate measure of the tendency of said petroleum oil to foul exposed heated metal surfaces, e.g., in processing. This ratio provides an indication of the incompatibility of the asphaltenes in the petroleum oil. It has been discovered that high aromatic/asphaltene ratio of a particular oil stream exhibit low fouling tendency. Conversely, a low aromatic/asphaltene ratio exhibits a high fouling tendency. This ratio provides an indication of the incompatibility of the asphaltenes in the petroleum oil. For example, a petroleum oil having a ratio above about 20 would be very low fouling. Generally, a ratio of from 0.1 to 19 would indicate high fouling oil.

In order to obtain the relationship between the ratio of aromatics/asphaltenes and fouling tendency a plurality of petroleum oils or resids were evaluated to determine their fouling tendency and the ratio of aromatics/asphaltenes for each which may be conveniently charted or plotted to provide a curve. Hence, some of the points for determining the fouling tendency at a given ratio may be interpolations between actual determinations. Any subsequent petroleum oil then need only have the ratio determined and the fouling tendency determined from a curve, chart or the like. Also, it is convenient to classify ranges of the ratios as high, medium, and low.

One aspect of the present invention is a method for determining the tendency of a petroleum oil to foul exposed heated surfaces comprising determining the amounts of total aromatics in said petroleum oil; determining the amount of asphaltenes in said oil; calculating the ratio of said amounts of total aromatics to asphaltenes; comparing said ratio to a previously determined tendency to foul for a petroleum oil with the same ratio or ratio range.

Alternatively, the ratio of saturated hydrocarbons to asphaltenes in the petroleum oil may be calculated and similarly compared to a previously determined tendency to foul for a petroleum oil with the same ratio. It will be appreciated that since the asphaltenes are less soluble in saturates, that low ratios would indicate low fouling, i.e., the opposite of the meaning of the aromatic/asphaltene ratio.

The specific methods of determining fouling tendency or the ratio of aromatics or saturates/asphaltenes are not critical, so long as they are reliable and reproducible.

Generally speaking, High Performance Liquid Chromatography (HPLC) may be used in regard to the present invention to separate and measure various fractions of deasphaltenated crude oils or other petroleum oils such residues. HPLC is described in the aforementioned U.S. Pat. No. 4,671,103.

HPLC separates successfully deasphaltenated crude oils into the three fractions that are the key in determining the crude composition. These fractions are: a saturate fraction, neutral aromatic fraction, and a polar aromatic fraction. The repeatability of the HPLC composition analysis is very good. Duplicate tests made on two crudes showed very good agreement.

HPLC systems are available in hundreds of different configurations from the basic, low cost single pump system to fully automated multi-solvent gradient systems.

The separations by HPLC are accomplished by pumping solvent/sample through a column which is packed with materials optimized for efficient separations. Separation results from differences in the extent to which the various components in the mixture interact with the column packing material. If there is little or no interaction, the component(s) will be retained in the column packing resulting in increasing elution time. Each component elutes from the column at a slightly different time, where it is detected and collected.

A basic HPLC unit is composed of a mobile phase reservoir, a pump for solvent delivery, a sample injector, a chromatography column. Efficiency of HPLC separation is achieved by using a combination of correct column, good HPLC apparatus, good operation and specialized know-how.

As mentioned previously, petroleum oils, such as crude oils and heavy hydrocarbons, are composed of two major parts; high molecular weight asphaltene (fraction insoluble in paraffinic solvents) and a lower molecular weigh asphaltene-free oil. The asphaltene and the oil fraction vary significantly in their chemical structure, coking characteristics, thermal characteristics, average molecular weight and distribution.

It has been found that fouling is primarily a compatibility problem of asphaltenes (defined herein as n-heptane insolubles or $C_7$-asphaltenes) with the other components of the oil. Hence, since asphaltenes are soluble in aromatics but generally insoluble in the saturated hydrocarbons, it is the amount of aromatics relative to asphaltenes that determines the compatibility notwithstanding the content of the saturates. Thus the type of oil is not of overall significance, e.g., crude, resid or otherwise. Hence, the aromatics/asphaltenes ratio as described above and the comparable fouling associated with the ratio in question may be determined on an actual crude or resid or on synthetic compositions. Subsequently, petroleum oils of any nature may have their aromatic/asphaltene ratio determined directly from the prior data. Thus it is not so much the relative amounts of saturates and aromatics but only the relative amount of aromatics and asphaltenes which controls and determines compatibility and hence fouling.

The aromatic content of the petroleum oil may be determined by techniques other than HPLC. For example, Nuclear Magnetic Resonance Spectroscopy (NMR) and/or quantitative analysis technique may be used to determine the quantity of aromatics in the petroleum oil.

The asphaltenes may be determined by insolubilization with antisolvents such as paraffinic solvents. Paraffinic and polar asphaltene antisolvents can be used and these are effective over a broad range of oil/solvent ratios. These antisolvents should be of low molecular weight, low viscosity and have low boiling characteristics to allow easy separation and recovery of the insolubles (asphaltenes).

The paraffin antisolvents are preferably up to $C_{10}$ straight or branched alkanes, usually $C_5$ to $C_{10}$. Suitable antisolvents include pentane, isopentane, hexane, 2-methyl hexane, n-heptane, octane, nonane, decane, isooctane and the like.

The paraffin antisolvents may include a small amount of a polar solvent material. The preferred polar antisolvents are organic compounds which are liquids under the conditions of use. The term "polar" refers to atoms such as oxygen, sulfur, oxygen halogens and nitrogen. A partial listing of suitable polar antisolvents includes alcohols such as, isobutanol, 2-pentanol, isoamyl alcohol; ketones such as acetone; methyl ethyl ketone; ethers such as diethyl ether, methyl propyl ether; esters such as methyl formate, butyl formate, methyl acetate, methyl propionate; glycol ethers, such as ethylene glycol monomethyl ether, ethylene glycol diethyl ether; heteroatom compounds such as furan, tetrahydrofuran, furfural, methyl pyridine, and the like. Mixtures of hydrocarbon and polar materials are desired antisolvents for petroleum streams containing functional groups.

Sufficient antisolvent is used to insolubilize the asphaltenes, generally about 1:10 to 1:100 (volume) sample to antisolvent. In the examples described in the aforementioned copending application Ser. No. 849,600, n-heptane was the solvent used to deasphaltenate the petroleum fraction. The asphaltene was determined by dissolving the total oil sample in n-heptane at a ratio of 1:40 at room temperature and filtering through 0.35 micron flurocarbon membrane. If desired asphaltenes extraction with the antisolvents can be made at higher temperature, e.g., 30°–100° C. Analytical methods other than liquid extraction with antisolvent can also be used for determining asphaltenes for example; claysilica gel chromatography and light scattering.

The effectiveness of the aromatic/asphaltene ratio as an indicator of the fouling tendency of the petroleum oil in question was described and exemplified in the aforementioned copending application Ser. No. 849,600. These tests demonstrated close correlation of aromatic-/asphaltene ratio data with TFT data.

B. Chromatographic Methods

As indicated above, the incompatible asphaltenes can also be determined by a technique based on Thin Layer Chromatography (TLC). The TLC technique is used to chromatographically separate the high molecular weight incompatible asphaltenes and the lower molecular weight oil fractions and compatible components. Thin layer chromatography is a well known technique as described in a book by Joseph C. Touchstone and M. F. Dobbins, entitled "Practice of Thin Layer Chromatography", published by Wiley-Interscience, 1978. The present invention, utilizes a modified form of TLC.

Thin layer chromatography is a separation method in which uniform thin layers of selected sorbent media are used as a carrier medium. The preferred sorbents are those which selectively separate the components by adsorption. The sorbent may be applied to a backing as a coating to obtain a stable layer of suitable size. The most common support is a glass plate, but other supports such as plastic sheets and aluminum foil are also used. The four sorbents most commonly used are silica gel, alumina, kieselguhr (diatomaceous earth), and cellulose. Silica gel (silicic acid) is the most popular material. It is slightly acidic in nature. A binding agent such as plaster of paris (calcium sulfate hemihydrate) is commonly used to secure the gel to the support.

As described in copending U.S. patent application Ser. No. 024,730, polymeric membranes may also be used. Separation can be accomplished in less than an hour at a very reasonable cost. Suitable membranes include polymeric porous membrane or film made from polymers containing polar atoms such as flourine, chlorine, oxygen, and nitrogen. Preferred membranes include those made from the group of polyvinylidine difluoride, polysulphone, cellulose acetate, and cellulose nitrate.

Fouling tendencies of the crude oil are indicated in the chromatographic medium by extreme differences in the migration of the molecularly light and heavy fractions on the TLC film (silica gel, polymer, membrane, etc.). These differences are shown by a clear demarcation between visually light and dark areas. Where heavy asphaltene fractions are incompatible with the lighter matrix oil, distinct dark colored ring or disk is formed as a result of the outward migration of the crude oil from the point of its deposition onto the chromatographic medium.

The crude oil is separated in a thin sorbent medium into respective molecularly light and heavy (asphaltenes) fractions, which are characterized by visually light and dark areas within the medium. The tendency of the crude oil to cause fouling in the refinery equipment is indicated by a visually distinct demarcation between the light and dark areas which dark area appears as a ring or disk.

A drop of the hydrocarbon stream to be tested is deposited on and thereby introduced into the thin layer chromatographic medium and fractionated by allowing the various fractions to migrate radially outwardly for a time sufficient to produce distinct demarcations between them. As previously discussed, the formation of a dark brown or black ring in the center of the medium will indicate the presence of incompatible high molecular weight asphaltenes which will have a tendency to cause fouling in conventional oil refinery operations.

The use of thin layer chromatography to separate the fractions of various fouling and non-fouling crude oils to identify the oil-asphaltene incompatibility provides a method capable of predicting by a quick and inexpensive test when a particular crude oil would foul the refinery equipment and lends itself readily to continual monitoring of the stream in accordance with one aspect of the present invention. This method for determining the fouling tendency of a particular oil can be corroborated by comparing the TLC results with those of the Thermal Fouling Tester for the same oil. Once corraborated, a standard curve, chart or fouling range classification can be established for comparing other TLC results. Also, it has been found convenient to establish an arbitrary numbering system based on known fouling tendencies, and to compare the result of the oil in question with such arbitrary scale to provide an indication of its fouling tendency.

As indicated earlier, oil-asphaltene incompatibility of the petroleum oil stream is indicative of the susceptibility of asphaltenes to separate from the oil, adhere to the heated metal surface, transfer into coke-like material and result in fouling of the metal surface. The greater the incompatibility of the asphaltenes in the oil, the high the fouling tendency of the hydrocarbon stream.

In most circumstances, it will be useful to enhance the TLC separation of the asphaltenes from the petroleum oil. This can be accomplished by dilution of the test sample of the hydrocarbon stream with a paraffinic solvent (asphaltene antisolvent) such as n-heptane, isooctane and hexane. The dilution with antisolvent can be varied from 1 to 3,000 percent based on the weight of the test sample. Oil sample/antisolvent volume ratios of 10:1 to 1:10 are preferred and ratios of 10:1 to 1:3 are most preferred. The mixture is then applied to the TLC film in the form of a drop. The antisolvent may also be applied to the film, in which case dilution of the sample may not be necessary. See aforementioned copending U.S. patent application Ser. No. 830,386 for a more detailed description of the antisolvent.

The following Examples are reported for illustrating the effectiveness of TLC in indicating incompatible asphaltenes in various crude oils.

Various crude oils were subjected to thin layer chromatography according to the following examples, the respective fouling tendencies identified by use of the above-referenced Thermal Fouling Tester.

A 10×10 cm silica gel coated glass plate was used. A drop of the crude oil or the fraction was dropped gently on the plate. The plate was allowed to stand at room temperature on a flat surface for from 45 minutes to 60 minutes. For light crude oils and fractions the separation was completed in a few minutes. For heavy crudes with very high viscosity such, the samples must be diluted to provide separation within 60 minutes.

The resulting chromatograms developed as a result of the placing of a drop of crude oil at the center of a silica gel film.

EXAMPLE 1

A sample of high fouling crude oil, and a light distillate of the same crude oil were each subjected to chromatographic separation at room temperature. After about one minute TLC chromatogram of the asphaltene containing high fouling showed distinctly the dark colored asphaltenes ring as a concentric ring in the chromatogram. The TLC chromatogram of an asphaltene-free distillate showed no presence of an asphaltene ring. This distillate of showed no fouling tendency as measured by the Thermal Fouling Tester (TFT).

EXAMPLE 2

A sample of the high fouling crude oil, Crude (BT) was modified by the addition of about 5 weight percent of asphaltenes (derived from Crude [BT]). A drop of the asphaltenated crude modification was subjected to chromatographic separation as described above. The resulting chromatogram was characterized by a dark asphaltene ring region inside a matrix region of the oil with compatible components.

Other examples of the effectiveness of TLC in providing an indication of fouling tendency are presented in the aforementioned U.S. patent applications Ser. Nos. 723,598; 830,386; 910,910; and 024,730.

The fouling tendency of several crude oil samples were determined (a) by the method described above using the apparatus described in U.S. patent application Ser. No. 910,910, and (b) by TFT. The following 0-100 scale was developed based on comparing the Apparatus reading and TFT readings.

| Fouling Tendency | Fouling Index of Apparatus | TFT T(°F.) |
|---|---|---|
| low | 0–20 | 0–15 |
| medium | 21–40 | 16–39 |
| high | 41–100 | 40+ |

The above scale was developed by calibrating the apparatus with TFT readings based on hundreds of samples.

The use of TLC in determining the tendency of hydrocarbon liquids to foul equipment correlate well with the tedious TFT method. Note that the apparatus reading does not correspond to the T of the TFT. However, the groupings (high, medium, low) correlated very well.

C. Operations

Ratio of Aromatics to Asphaltene Method: A sample of petroleum oil up stream of the equipment being protected is taken and deasphaltenated and subjected to HPLC for determination of the aromatics. The initial fouling tendency of the oil is determined and antifoulant treatment rate is established. The asphaltenes are determined and the weight ratio of the aromatics to asphaltenes determined. The ratio is converted into an electric signal and transmitted to the pump used to introduce antifoulant chemical into the stream. The chemical injection thus is made automatically responsive to changes in the fouling tendency of petroleum oil. For a low ratio (high fouling oil), the rate of antifoulant chemical will be decreased. For a high ratio, chemical injection will be increased. Sampling preferably is at frequent time intervals (every 1-12 times per day) but not less than once a day.

TLC Method: The sampling point in this method may be upstream of the heat exchanger or at any convenient location near the stream entrance of the refinery. The initial fouling tendency may be determined and the antifoulant treatment rate established.

Oil samples from the inlet stream are taken at frequent intervals but not less than once a day, preferably between 1 and 12 times a day, and most preferably than between 2 and 12 times a day. The samples are run by the TLC method described herein, which normally requires from 30 to 60 minutes to complete. If a change in the incompatibility of the hydrocarbon oil stream is determined, the treatment of the antifoulant is automatically adjusted. Although the adjustment lags the sampling by the time required to develop the chromatograph, the response time (e.g. 30-60 minutes), is adequate particularly for the same oil, since incompatible asphaltenes do not change drastically in such short time intervals.

The antifoulant useable for the above methods include any capable of reducing asphaltene fouling such as organic polymeric dispersants. Such disperants are sold under Exxon Chemicals as trade designations COREXIT 225 and COREXIT 241. A preferred antifoulant is polyisobutylene succinic anhydride condensed with polyethyleneamine described in copending U.S. patent application Ser. No. 050,119, filed May 15, 1987, adandoned Jun. 8, 1988 the disclosure of which is incorporated herein by reference.

APPARATUS

While the method for practicing the present invention is described in general terms, the apparatus constructed according to the present invention is based on TLC techniques. The apparatus comprises (a) a sampling assembly for obtaining representative samples from the oil stream; (b) a detector for determining incompatible asphaltenes in a hydrocarbon oil stream (detector); (c) means for introducing an antifoulant (e.g. antifoulant injector) into the hydrocarbon oil stream; and (d) means for operating the antifoulant injector in response to the detector indicating the fouling level reaching or exceeding a predetermined level (e.g. a level which treatment is required for protection against fouling). It is preferred that the detector apparatus further include a mixing chamber for mixing the oil sample with an antifoulant.

As illustrated in FIG. 1, the sampling assembly 10 receives a sample of a hydrocarbon oil stream such as a crude oil feed stream 11 to a refinery via line 12. The sample is delivered to a detector 13 which determines the presence of incompatible asphaltenes and sends an electrical signal via conductor 14 representative thereof to operate the injector assembly 15. The injector assembly 15 may take a variety of forms, including an electric driven pump 16, electric controls 17 connected to the pump motor, and a tank 18 for containing liquid antifoulant. Tank 18 is connected to the suction and the pump discharge is connected to the crude feed line 11 by line 19. The controls 17 receive the signal from detector 13 and operates the motor of pump 16.

In operation a sample of the feed stream is diverted to the sampling assembly 10 which at predetermined time intervals and delivers a sample to the detector 13. The sample line 12 may include a return line and a pump for continuously circulationg crude oil through line 12. Thus, a sample from the line will be representative of the feed stream at the time of sampling. However, the volume of the sample diverted from line 13 is small such that a control valve 30 (See FIG. 3) may be employed in line 12 and actuated to permit diversion of sample to the sampler and closed to interrupt flow. The detector 13 determines the level of incompatible asphaltenes in the crude oil and sends an electric signal representative thereof to the electric controls 17. If the incompatible asphaltenes exceeds a predetermined level, this condition is sensed and the signal to the controls operates the pump motor causing the pump 16 to feed antifoulant to the feed stream 11 via line 19.

Figure 2:
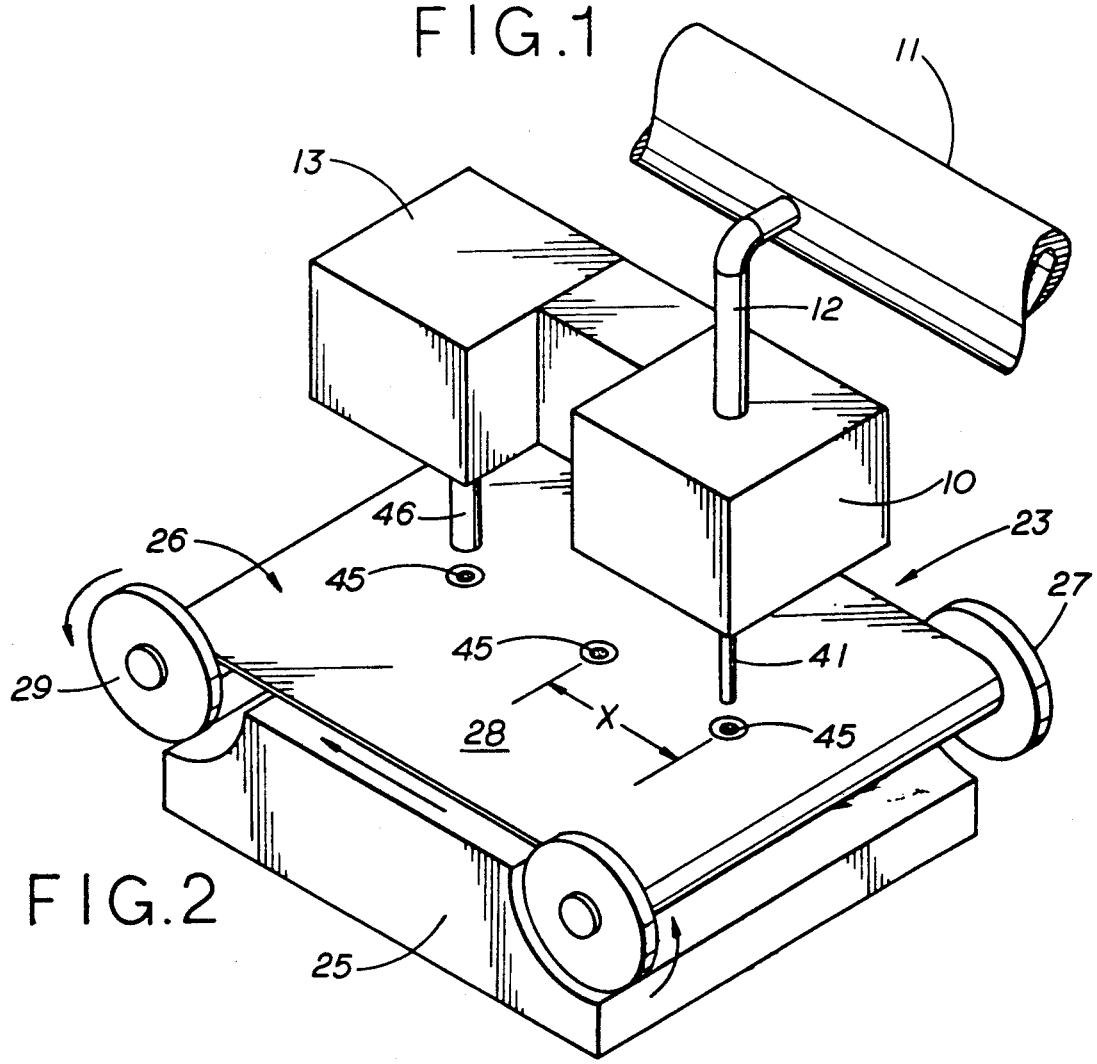
FIG. 2 is a schematic illustrating one embodiment of the sampling and analyzer portion of the apparatus for practicing the invention.

FIG. 2 is also a schematic but presents more details, of the sampling assembly 10 and detector 13. The sampling assembly 10 receives the crude oil from the feed stream 11 through sample line 12 and delivers a drop of the sample onto an underlying film assembly 23, which moves the drop into alignment with the detector 13.

The film assembly 23 includes a film 26 which is capable of chromatographically separating the hydrocarbon oil drop in the manner described above. Preferred films include silica gel deposited on a flexible substrate and most preferably a membrane such as that disclosed in the aforementioned copending application U.S. Ser. NO. 024,730. The film 26 is mounted on a storage reel 27, extending through a flat horizontal section 28 and to take up reel 29. Flat section 28 underlies assemblies 10 and 13. The takeup reel 29 is driven in increments and serves to index the film at predetermined time intervals and lengths. The storage reel 27 may be free wheeling whereas the takeup reel 16 is driven as for example by a ratchet mechanism similar to a camera. The film assembly 23 thus provides three important functions: (1) means for receiving the sample drop, (2) chromatographic development of the sample drop; and (3) movement of the sample into alignment with the detector 13.

As indicated above, the sampling assembly 10 obtains a representative sample from the oil stream and delivers a drop on to the underlying film 26. It will be obvious to those skilled in the art that the assembly 10 can take a variety of forms provided that it functions to deposit a representative sample of the oil unto the horizontal section 28 of the film 26 with minimum disturbance.

A variety of devices such as pneumatically or electrically actuated syringes may be used to deliver the drop to the underlying film. It's important that each drop have approximately the same volume.

Figure 3:
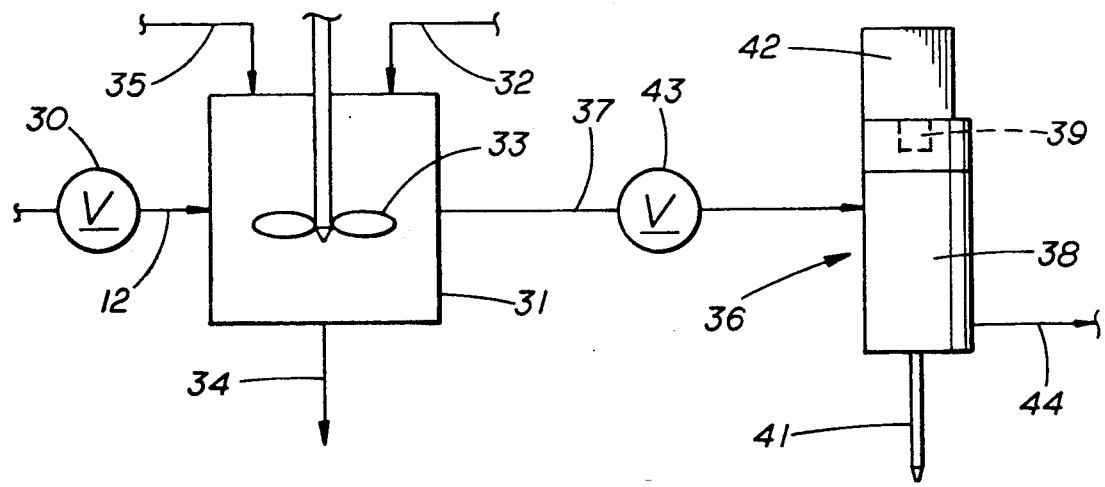
FIG. 3 is a schematic diagram of an injector assembly useable in the present invention.

FIG. 3 schematically depicts but one type of sampling assembly useable to deposit a drop onto film 26. The sampling assembly 10, includes a mixing chamber 31, which receives the oil sample from line 12. Antisolvent may be introduced into chamber 31 via line 32, and rotary mixer 33 intermixes the sample and antisolvent. A gas (i.e. nitrogen) purge line 35 also discharges into chamber 31. The chamber 31 may be provided with drain line 34. The chamber may have a volume of 50 to 200 cc to receive both the sample and antisolvent.

The mixing chamber 31 is connected to a injector 36 via line 37. If the chamber 31 is not pressurized, a small pump may be provided in line 37 to transfer the mixed sample to the injector 36. Injector 36 includes a tubular body 38 having a plunger 39 mounted in the upper end thereof and a needle injector 41 (e.g. 16-20 gauge metal needle) at its lower end. The plunger 39 may be driven through an injector stroke via solenoid 42 (or diaphragm if pneumatic). Valve 43 may be used to close the inlet to body 38 during the injection stroke of the plunger 39. Actuation of the solenoid 42 moves the plunger 39 through a precise stroke to deliver one drop from needle 41 unto the underlying film (See FIG. 2). Line 44 located at the bottom of body 36 serves to purge the sample following the sampling cycle.

Returning to FIG. 2, the sample drop falls a short distance from needle 41, in the order of $\frac{1}{8}$ inch, onto the chromatographic film 26 and the film is advanced an incremental amount. The oil samples on the film 26 are illustrated by reference numerals 45 in FIG. 2. It should be observed that the film 26 should remain in the horizontal disposition for a sufficient period of time to achieve chromatographic separation of the incompatible asphaltenes of the crude oil as described in detail in aforementioned copending U.S. patent application Ser. Nos. 910,910 and 024,730. Time increments will depend on the nature of the sample and whether or not antisolvents are used. Time intervals from fifteen to ninety minutes, preferably thirty to sixty minutes, should be satisfactory for most samples. The film advancement usually is a short distance illustrated by X in FIG. 2. With the chromatogram fully developed, the film is indexed to bring it into vertical alignment with the detector 13. The detector may be an analyzer of the type described in the aforementioned copending U.S. patent application Ser. No. 910,910 and U.S. patent application Ser. No. 024,730. The analyzer includes a light source, means for moving the light source to scan the sample drop 45 positioned underneath the assembly, means for measuring transmitted or reflected light, as the case may be, with respect to sample 45; and means for converting the reflected or transmitted light into an electric signal representative thereof. The light source and light receiver may be incorporated into a scanner, a portion of which is illustrated as 46 in FIGS. 2 and 4. In a preferred embodiment, the analyzer includes means for comparing light reflected by the asphaltene ring that of the matrix. The scanner of assembly 22 shown as 41 in FIG. 3 is the electrical signal is transmitted to the pump assembly.

Following completion of the sampling and injection cycle, the system may be purged preparatory for receiving the next sample.

Figure 4:
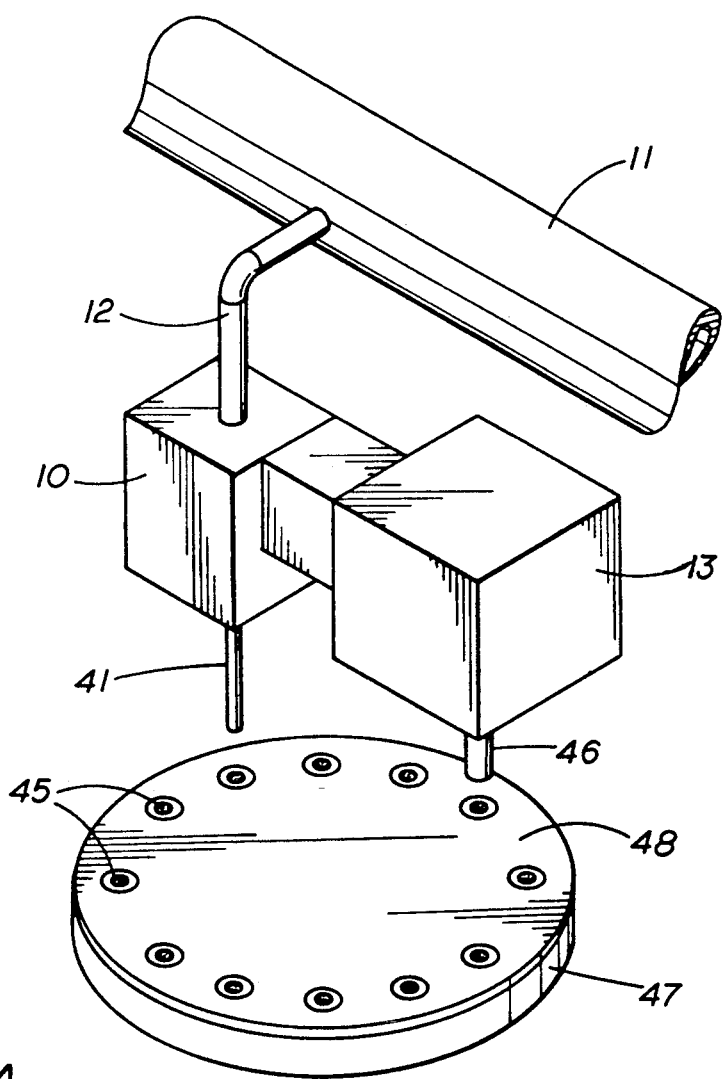
FIG. 4 is another embodiment of the sampling and analyzer portion of the invention.

FIG. 4 illustrates another embodiment of the invention, which is particularly adapted to employ rigid films such as TLC glass plates. In this embodiment, the sampling assembly 10 and detector 13 may be the same as those depicted in FIGS. 2 and 3.

The moveable film assembly includes a disc 47 on which may be mounted a TLC glass plate 48. The disc 47 may be mounted on a vertical shaft which is driven by ratchet means to turn the shaft and hence the disc in radial increments. The ratchet means may be mounted and electrically driven. These types of mechanisms are familiar to those skilled in the art.

Disc 47 and hence the film 48 are maintained in a substantially horizontal position with the sampling assembly 10 disposed thereover such that the drops from needle 41 are deposited on the film 48, afterwhich the disc 47 and the film 48 are turned a predetermined amount, placing the assembly in position for receiving the next drop. Indexing the disc 47 a predetermined number of times, brings the sample 45 into alignment with the scanner 46 of detector 10 which may be the same as described previously. Note that the chromatogram must be substantially fully developed by the time it reaches the scanning position.

The intensity and area of the asphaltene ring, when optically compared to the sample in the TLC film matrix provides a reliable indication of the fouling tendency of the liquid hydrocarbon. The optical data is converted to logic level pulse representative of the light reflected. These signals during each scan provides a profile of the liquid hydrocarbon sample. By integrating the area of the profile corresponding to the asphaltene separated portion (matrix profile being 0) the characteristic reading of the samples tendency to foul is obtained. This value is compared to a standard value of hydrocarbons, and an electric signal representative thereof is transmitted to the pump controls.

In summary, the present invention relies on the ability of the analytical techniques to determine asphaltene incompatibility in a relatively short period of time. This permits frequent monitoring on a continual basis and frequent adjustment of antifoulant to maintain optimum treating rates over variable fouling conditions. It will be apparent to those skilled in the art that a modifications and variations of the embodiments described herein are possible without departing from the principles of the invention.

What is claimed is:

1. A method of treating a crude oil stream containing incompatible fouling asphaltenes wherein an antifoulant is introduced into said stream which comprises
   (a) continually obtaining a sample from said stream at frequent time intervals;
   (b) for each sample obtained measuring a property of the sample which is indicative of the incompatible asphaltenes therein; and
   (c) adjusting the introduction of the antifoulant in response to changes in the level of incompatible asphaltenes in the samples as indicated in step (b).

2. The method of claim 1 wherein the sample is first mixed with an antisolvent before measurement of said property.

3. the method as defined in claim 1 wherein the measuring step comprises
   (i) depositing a portion of each sample of the oil stream onto a surface of a thin film made up of a chromatographic separation material;
   (ii) letting the sample of the liquid hydrocarbon migrate
   (iii) letting the sample of liquid hydrocarbon migrate radially outward within said film for sufficient time so that hydrocarbon compatible fractions in the same separate from any hydrocarbon-incompatible asphaltenes in the sample, wherein said hydrocarbon compatible fractions form a matrix portion in the film and any hydrocarbon-incompatible fractions form a dark ring within the matrix portion and wherein any ring formed is disposed within a central region of the matrix portion and is distinguished from the matrix portion by a dark area having a boundary with respect to a lighter area; and (iv) determining the tendency of the liquid hydrocarbon stream to foul equipment by comparing the matrix portion with any dark ring formed from any hydrocarbon-incompatible asphaltenes in the sample, wherein the area and intensity of any ring formed in relation to the matrix portions provides an indication of the tendency of the liquid hydrocarbon stream to foul equipment.

4. The method of claim 3 wherein the film is a polymeric membrane capable of chromatographic separation of incompatible asphaltenes from compatible components of the sample.

* * * * *